(12) United States Patent
Thursby et al.

(10) Patent No.: US 10,545,330 B2
(45) Date of Patent: Jan. 28, 2020

(54) INSPECTION ASSEMBLY

(71) Applicant: E.V. OFFSHORE LIMITED, Norwich (GB)

(72) Inventors: Jonathan Thursby, Norwich (GB); Shaun Peck, Oulton Broad (GB)

(73) Assignee: E.V. OFFSHORE LIMITED (GB)

( * ) Notice: Subject to any disclaimer, the term of this patent is extended or adjusted under 35 U.S.C. 154(b) by 0 days.

(21) Appl. No.: 16/062,413

(22) PCT Filed: Dec. 13, 2016

(86) PCT No.: PCT/GB2016/053923
§ 371 (c)(1),
(2) Date: Jun. 14, 2018

(87) PCT Pub. No.: WO2017/103579
PCT Pub. Date: Jun. 22, 2017

(65) Prior Publication Data
US 2018/0373019 A1 Dec. 27, 2018

(30) Foreign Application Priority Data
Dec. 15, 2015 (GB) .................................. 1522066.8

(51) Int. Cl.
*G02B 13/06* (2006.01)
*G02B 23/24* (2006.01)
*G01N 21/954* (2006.01)

(52) U.S. Cl.
CPC ....... *G02B 23/2469* (2013.01); *G01N 21/954* (2013.01); *G02B 23/2423* (2013.01);
(Continued)

(58) Field of Classification Search
CPC ............... G01N 21/6458; G01N 21/65; G01N 21/6428; G01N 2021/656; G01N 2201/08;
(Continued)

(56) References Cited

U.S. PATENT DOCUMENTS 6,333,826 B1 * 12/2001 Charles .................. G02B 13/06
359/725
6,654,116 B1 * 11/2003 Kwirandt ............. G01N 21/909
209/524
(Continued)

FOREIGN PATENT DOCUMENTS

GB 2500671 A 10/2013
JP H10239596 A 9/1998
(Continued)

*Primary Examiner* — Michael P Stafira
(74) *Attorney, Agent, or Firm* — Hayes Soloway PC

(57) ABSTRACT

This invention relates to an inspection assembly comprising a light source and a lens. In particular this invention relates to the provision of a reflection surface for improving the illumination of a field of view of a wide angle camera. An inspection assembly comprises a main body having a longitudinal axis and a distal end; a lens located at the distal end; a light source positioned to illuminate an area beyond the distal end of the main body; and a reflection surface, an angle between the reflection surface and the longitudinal axis of the main body being between 10° and 70°, wherein the reflection surface is positioned such that, in use, a first fraction of the light emitted by the light source is reflected by the reflection surface and a second fraction of the light emitted by the light source travels to an area beyond the distal end of the main body without being reflected by said surface.

15 Claims, 3 Drawing Sheets

(52) U.S. Cl.
CPC . *G02B 23/2484* (2013.01); *G01N 2021/9544* (2013.01); *G02B 13/06* (2013.01)

(58) Field of Classification Search
CPC .......... G01N 2021/653; G01N 21/211; G01N 21/4738; G01N 21/6456; G01N 2021/3144; G01N 2021/6419; G01N 2021/6421; G01N 2021/6423; G01N 2021/651; G01N 21/474; G01N 21/4795; G01N 21/6408; G01N 21/645; G01N 21/648; G01N 2201/064; G01N 2201/065; G01N 2291/056; G01N 29/0618; G01N 29/0645; G01N 15/1434; G01N 2021/4797; G01N 21/1702; G01N 21/21; G01N 21/3581; G01N 21/3586; G01N 21/49; G01N 21/64; G01N 21/6452; G01N 21/8806; G01N 21/94; G01N 21/9501; G01N 2201/0636; G01N 2201/0655; G01N 2201/068; G01N 2291/044; G01N 2291/102; G01N 2291/106; G01N 29/0609; G01N 29/07; G01N 29/11; G01N 29/223; G01N 29/2487; G01N 29/262; G01N 33/551; G02B 19/0023; G02B 19/0033; G02B 21/0056; G02B 21/008; G02B 21/02; G02B 21/0032; G02B 21/0092; G02B 21/082; G02B 21/16; G02B 6/32; G02B 19/0019; G02B 21/002; G02B 21/0036; G02B 21/006; G02B 21/04; G02B 21/10; G02B 21/361; G02B 6/102; G02B 6/262; G02B 21/0004; G02B 21/0008; G02B 21/0024; G02B 21/0028; G02B 21/0076; G02B 21/06; G02B 21/14; G02B 21/26; G02B 21/36; G02B 23/2423; G02B 23/2453; G02B 26/001; G02B 26/0816; G02B 26/0833; G02B 26/101; G02B 26/103; G02B 26/105; G02B 26/108; G02B 27/0025; G02B 27/0093; G02B 27/09; G02B 27/1066; G02B 27/40; G02B 27/58; G02B 3/0087; G02B 6/12007; G02B 6/124; G01J 3/0216; G01J 3/021; G01J 3/0218; G01J 3/10; G01J 3/32; G01J 3/36; G01J 3/44; G01J 3/4406; G01J 4/00; G01J 1/4257; G01J 3/0221; G01J 3/024; G01J 3/26; G01J 3/28; G01J 5/0825; G01J 5/0837

See application file for complete search history.

(56) References Cited

U.S. PATENT DOCUMENTS

| | | | |
|---|---|---|---|
| 2003/0218684 A1* | 11/2003 | Horiguchi | G02B 13/06 348/335 |
| 2006/0023105 A1* | 2/2006 | Kostrzewski | G06T 3/0018 348/335 |
| 2007/0217042 A1* | 9/2007 | Kweon | G02B 5/10 359/850 |
| 2008/0045797 A1 | 2/2008 | Yasushi et al. | |
| 2008/0143822 A1 | 6/2008 | Wang et al. | |
| 2013/0016178 A1* | 1/2013 | Birkbeck | H04N 5/2254 348/36 |
| 2014/0347878 A1 | 11/2014 | Honda et al. | |

FOREIGN PATENT DOCUMENTS

| | | |
|---|---|---|
| JP | 2002014292 A | 1/2002 |
| JP | 2002040335 A | 2/2002 |
| JP | 2010055023 A | 3/2010 |
| JP | 2012090723 A | 5/2012 |
| JP | 2013029582 A | 2/2013 |
| WO | 2012170401 A2 | 12/2012 |

\* cited by examiner

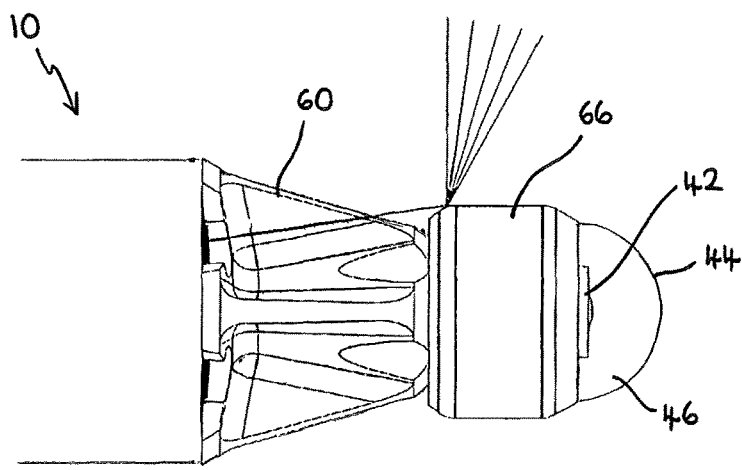
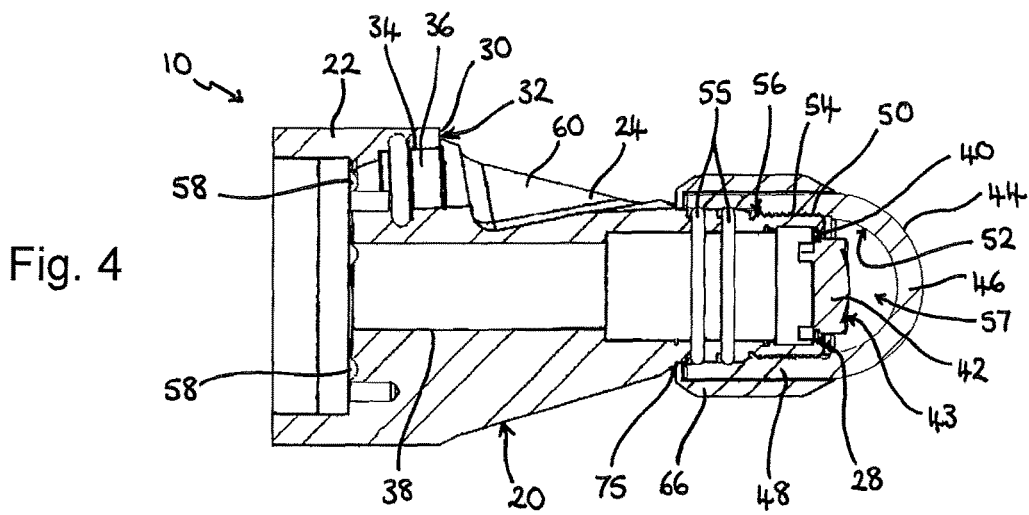
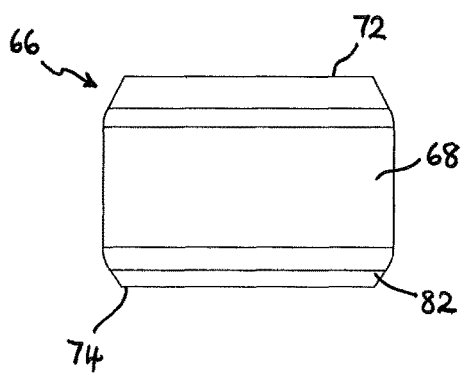
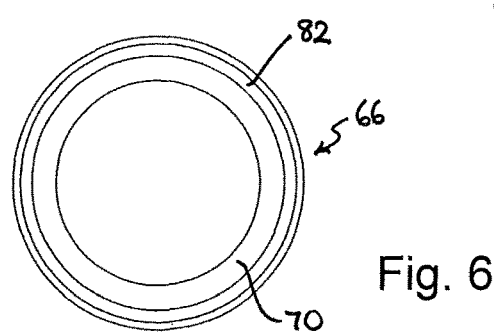
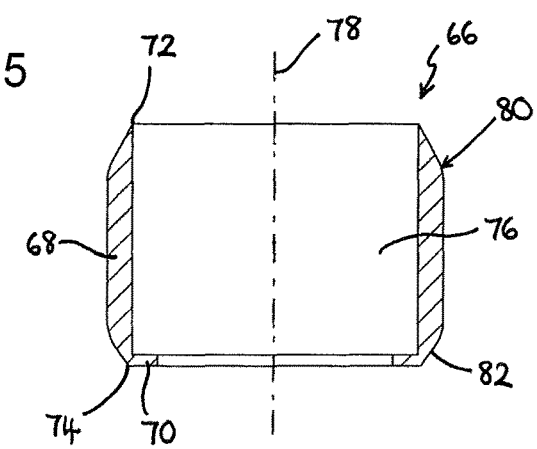

INSPECTION ASSEMBLY

BACKGROUND a. Field of the Invention

This invention relates to an inspection assembly comprising a light source and a lens. In particular this invention relates to the provision of a reflection surface for improving the illumination of a field of view of a wide angle camera. This invention further relates to a reflection collar and a method of illuminating a structure. The invention is particularly suited to inspection systems and camera systems that operate downhole, in pipelines or in other internal spaces.

b. Related Art

Systems and assemblies for inspecting internal spaces such as interior walls of pipelines or similar are known. When these systems are used downhole, for example in offshore environments, an inspection assembly comprising a source of illumination and a camera are lowered through the pipeline or conduit and the camera is configured to capture images of the internal surfaces of the pipeline. In this way the inspection system may be used to visualise the condition of the pipeline to determine if remedial action is required.

In some of these inspection systems the camera is located in a nose region of the assembly and is forward facing. In this way, the camera is able to capture images of the interior of the pipeline ahead of the inspection assembly as it is lowered or moved through the pipeline.

In order to provide even illumination of the field of view of the camera, the light sources are often located behind the camera lens and are angled in a direction towards the internal wall of the pipeline ahead of the inspection assembly. In this way the walls of the pipeline are illuminated at a distance from the front of the inspection assembly.

In some systems it is desirable to use a wide angle lens, such as a fish-eye lens. When existing systems are retrofitted with such a wide angle lens, however, the configuration of the light sources is such that there is inadequate illumination of the entire field of view. In particular the periphery of the image tends to be under exposed and the central portion of the image tends to be over exposed.

It is, therefore, an object of the present invention to provide an improved illumination system that may be used, in particular, with camera systems incorporating a wide angle lens.

SUMMARY OF THE INVENTION

According to a first aspect of the present invention there is provided an inspection assembly comprising:
a main body having a longitudinal axis and a distal end;
a lens located at the distal end;
a light source positioned to illuminate an area beyond the distal end of the main body; and
a reflection surface, an angle between the reflection surface and the longitudinal axis of the main body being between 10° and 70°,
wherein the reflection surface is positioned such that, in use, a first fraction of the light emitted by the light source is reflected by the reflection surface and a second fraction of the light emitted by the light source travels to an area beyond the distal end of the main body without being reflected by said surface.

The location of the reflection surface, therefore, causes a part of the light beam from the light source to be deflected such that an angle between the direction of travel of the deflected light beam and the longitudinal axis is greater than the angle between the direction of travel of the non-deflected light beam and the longitudinal axis.

When the inspection assembly is located in a pipeline or conduit, the fraction of the emitted light that is deflected or reflected, therefore, illuminates a region of the interior walls of the pipeline closer to the inspection assembly. This creates a more even illumination of the field of view if a wide angle lens is used in the inspection assembly.

In preferred embodiments the angle between the reflection surface and the longitudinal axis of the main body is between 30° and 40°.

In order to still provide adequate illumination of the central region of the field of view, however, it is preferable if the first fraction is less than 50% of the emitted light.

In preferred embodiments of the inspection assembly a plurality of light sources is arranged around the main body and positioned radially outward of the lens. Furthermore, in particularly preferred embodiments an annular reflection surface extends around the main body. In this way, even illumination may be provided around the complete periphery of the field of view.

The light source or each of the light sources is preferably located at a distance from the lens along the longitudinal axis. In particular the light source or light sources may be located at a distance behind the lens, i.e. further from the distal end of the inspection assembly. In these embodiments the reflection surface is preferably located between the light source(s) and the lens.

The inspection assembly of the present invention has particular advantages when the lens is a wide angle lens. In some embodiments the lens may be an ultra wide angle lens, such as a fish-eye lens. In these embodiments the reflected light illuminates the periphery of the field of view while the emitted light that is not reflected illuminates central regions of the field of view.

To protect the lens from the environment of the pipeline a transparent window or cap is preferably positioned to extend over the lens. In embodiments in which a wide angle lens is used the window is preferably dome-shaped. In these assemblies, the reflection surface is located such that the first fraction of the emitted light is reflected in a direction substantially away from the window. As such, the likelihood of light directly entering the window and being internally reflected or refracted is significantly reduced.

The reflection surface is preferably part of a reflection collar attached to the main body of the assembly. The collar is typically made of a metal material and the reflection surface is preferably an unpolished surface of the collar.

The reflection surface is preferably configured to cause diffuse reflection of the emitted light striking the reflection surface. This creates more even illumination of the field of view of the lens and allows the reflected light to illuminate a greater area.

The inspection assembly preferably further comprises an image sensor arranged to capture an image of a field of view through the lens. The inspection assembly may additionally include a memory for storing the captured image data or a transmitter for transmitting the image data to a remote receiver in real time.

According to a second aspect of the present invention there is provided a reflection collar for an inspection assembly, the reflection collar comprising:

a sleeve portion having first and second ends defining an axis of the collar, and a bore for receiving a part of the inspection assembly;

means for retaining the reflection collar in a fixed position relative to the inspection assembly; and a reflection surface, an angle between the reflection surface and the axis of the collar being between 10° and 70°.

In use, the collar is preferably retained on the inspection assembly such that the first end of the sleeve portion is nearer a distal end of the inspection assembly. The reflection surface is preferably located proximate the second end of the sleeve portion. Accordingly, the reflection surface may be facing in a direction substantially away from the distal end of the assembly when the collar is installed. Preferably a region of the external surface of the sleeve portion, at the first end of the sleeve portion, is tapered.

The collar is preferably made of a metal material and the reflection surface is an unpolished surface.

Typically the collar is substantially tubular and an external diameter of the collar is preferably between 25 mm and 35 mm.

According to a third aspect of the present invention there is provided a method of illuminating an area, the method comprising:

illuminating a light source to produce a beam of light; and locating a reflector surface in the beam of light such that a first fraction of the light emitted by the light source is reflected by the reflection surface and a second fraction of the light emitted by the light source passes the reflection surface without being reflected by said surface.

In preferred embodiments an inspection assembly includes a plurality of light sources and the method preferably comprises illuminating an annular arrangement of light sources, and locating an annular reflector surface such that a first fraction of the light emitted by the light sources is reflected by the reflection surface. An outer perimeter of the annular reflector surface is preferably located radially inward of centre lines of the beams of light emitted by the light sources.

The or each light source emits light substantially in a first direction defined by a centre line of the beam of light from said light source. In order to achieve the desired illumination, an angle between the reflection surface and the centre line of the beam of light is preferably between 10° and 70° and more preferably between 25° and 50°.

BRIEF DESCRIPTION OF THE DRAWINGS

The invention will now be further described by way of example only and with reference to the accompanying drawings, in which:

FIG. 3 is a side view of a distal end region of the inspection assembly of FIG. 1 showing reflection and diffusion of a light beam striking the reflection collar;

FIG. 4 is a cross sectional view of an end of the inspection assembly of FIG. 1 showing the position of the reflection collar with respect to the light source and camera lens of the inspection assembly;

FIG. 5 is a side view of the reflection collar of FIG. 1;

FIG. 6 is an end view from a second end of the reflection collar of FIG. 5;

FIG. 7 is a longitudinal sectional view of the reflection collar of FIG. 5;

DETAILED DESCRIPTION

Figure 1:
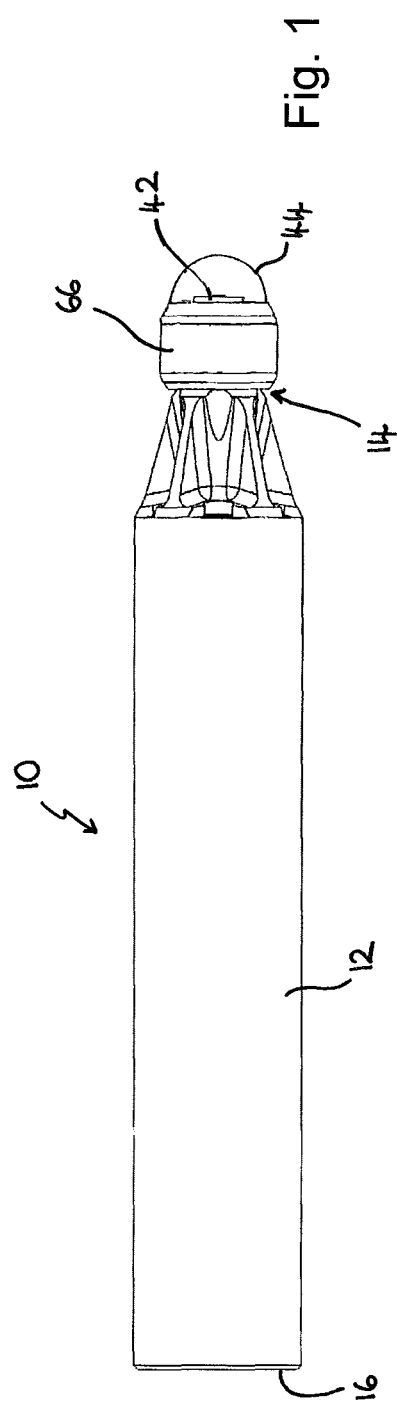
FIG. 1 is a side view of an inspection assembly including a reflection collar according to a preferred embodiment of the present invention.

Inspection assemblies or camera systems used to inspect passageways such as pipelines and wellbores typically include a camera and one or more light sources arranged to light the field of view of the camera. Typically these are housed in a first, distal end region of an elongate cylindrical housing which is lowered down the wellbore by cables or a shaft attached at a second end. In most cases, the camera systems will also include a viewport or window at or near the distal end of the camera housing that serves to protect the camera.

In use, when an inspection assembly is deployed along a passageway, the distal end of the assembly will be a front end with respect to a direction of travel of the assembly. Accordingly, in the following description the terms front end, forward facing or similar will be used to describe or refer to elements that are located at or near the first, distal end of the assembly or that face in a direction towards the distal end. Similarly, the terms rear end, rearward facing or similar denote elements that are located at or near the second, proximal end of the assembly or that face in a direction towards the second end.

A preferred embodiment of an inspection assembly 10 according to the present invention is illustrated in FIGS. 1 to 4. The inspection assembly 10 includes an elongate main body 12 having a first, distal end 14 and a second, proximal end 16. The first and second ends 14, 16 define a longitudinal axis 18 of the inspection assembly 10.

An end region 20 of the main body 12 at the distal end 14 comprises a light emitting portion 22, a light guide portion 24 and a nose portion 26. The nose portion 26 includes a distal end face 28 of the main body 12. The end region 20 is generally tapered such that an external diameter of the main body 12 at the light emitting portion 22 is greater than the external diameter of the nose portion 26.

A decrease in diameter of the light emitting portion 22 creates a shoulder 30 having a generally forward facing surface 32. A plurality of apertures 34 are formed in the shoulder 30. The apertures 34 are sealed by transparent windows or viewports 36. The apertures 34 are preferably in a substantially circular or annular arrangement around the shoulder 30.

Figure 2:
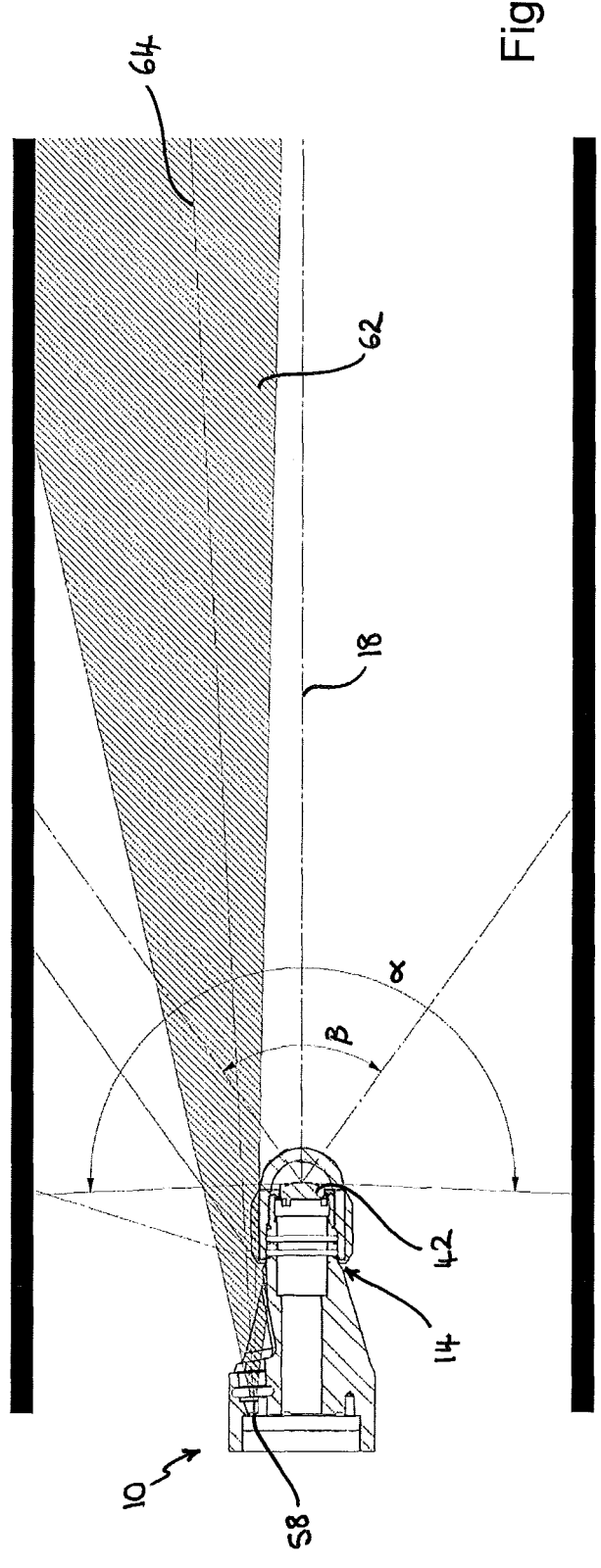
FIG. 2 shows the inspection assembly of FIG. 1 in a passageway and illustrates a field of view of a camera and a region of illumination of a light source of the inspection assembly.

A bore 38 extends longitudinally through the end region 20 and terminates at an aperture 40 in the distal end face 28. A lens 42 is mounted in the aperture 40. The lens 42 is preferably an ultra wide angle lens such as a fish-eye lens. The fish-eye lens will typically have an angle of view ($\alpha$) of about 185°, compared to a standard lens having an angle of view ($\beta$) of about 74°, as illustrated in FIG. 2. In this embodiment, including a fish-eye lens 42, a part of the lens 42 projects forward of the distal end face 28 so that the angle of view or field of view is not obstructed by the end face 28 of the main body 12.

The inspection assembly 10 further comprises a camera including an image sensor arranged to capture an image of the field of view through the lens 42. Accordingly, the camera captures an image of a region substantially ahead or in front of the distal end 14 of the inspection assembly 10. It will be appreciated that if an ultra wide angle lens 42 is used, having an angle of view of greater than 180°, the periphery of the image may include a region located substantially parallel with or a small distance behind the distal end face 28 of the inspection assembly 10.

To protect the lens 42, the inspection assembly 10 includes a cap 44, shown most clearly in FIG. 4. The cap 44 comprises a hemi-spherical or dome-shaped window portion 46 and a tubular attachment portion 48. At least the window portion 46 is optically transparent. Typically the cap 44 will be a unitary piece such that both the window portion and the attachment portion are made of the same transparent material. Preferably the cap 44 is made of a suitable acrylic material.

The attachment portion 48 includes a female securing feature in the form of a screw thread 50 on an internal surface 52 of the attachment portion 48. A corresponding male securing feature in the form of a screw thread 54 is provided on an external surface 56 of the nose portion 26 of the main body 12. The cap 44 is, therefore, secured to the main body 12 by engaging the complementary screw threads 50, 54. Once engaged, the attachment portion 48 of the cap 44 extends around the nose portion 26 of the main body 12. Sealing elements such as o-rings 55 may be provided to form a seal between the external surface 56 of the nose portion 26 and the internal surface 52 of the cap 44.

With the cap 44 secured to the main body 12 the window portion 46 extends beyond the distal end face 28 of the nose portion 26. In particular the domed window portion 46 extends over the lens 42 such that there is a gap 57 between a front face 43 of the lens 42 and the internal surface 52 of the window portion 46 of the cap 44.

The inspection assembly 10 further comprises a plurality of light sources 58 mounted in the light emitting portion 22 of the main body 12. The light sources 58 are preferably light emitting diodes (LEDs). Each of the light sources 58 is arranged to emit a beam of light through a corresponding one of the apertures 34. As such, the light sources 58 are substantially forward facing and the light emitted by the light sources 58 travels in a direction that illuminates an area ahead of or in front of the distal end 14 of the inspection assembly 10.

The light guide portion 24 of the end region 20 comprises a plurality of radially extending webs or ribs 60. Light guide channels are defined between neighbouring ribs 60. Each channel is aligned with one of the apertures 34.

As shown in FIG. 2, each light source 58 emits a diverging beam of light 62. A direction of the emitted light is defined by a centre line 64 of the light beam 62. The beam divergence angle is preferably between 10° and 30°, and most preferably about 20°.

A reflection collar 66 is located over and around the attachment portion 48 of the cap 44. As shown in FIGS. 5 to 7, the collar 66 comprises a sleeve portion 68 and retaining means in the form of a retaining flange 70. The sleeve portion 68 is substantially tubular and extends between first and second ends 72, 74. A bore 76 of the sleeve portion 68 extends along an axis 78 of the collar 66. The retaining flange 70 projects radially inwardly from the second end 74 of the sleeve portion 68.

In a preferred embodiment the collar 66 has a circular cross-sectional shape. An internal diameter of the sleeve portion 68 is constant along the length of the sleeve portion 68 and is sized to receive the attachment portion 48 of the cap 44. An external surface 80 of the collar 66 at the first end 72 is tapered.

The external surface 80 of the collar 66 is also tapered at the second end 74. This tapered portion of the surface 80 provides a reflection surface 82. An angle between the reflection surface 82 and the axis 78 of the collar 66 is preferably greater than 10° and less than 70°. The angle between the reflection surface 82 and the axis 78 may be more than 20° or more than 30°. The angle between the reflection surface 82 and the axis 78 may be less than 60°, less than 50° or less than 40°. Most preferably the angle is between 30° and 40° and will typically be about 36°.

The collar 66 is preferably made from a metallic material, and will typically be made from a suitable grade of stainless steel. The reflection surface 82 is preferably unpolished. This causes the light that is reflected from the surface 82 to be diffused, as illustrated in FIG. 3.

To attach the reflection collar 66 to the main body 12 of the inspection assembly 10, the collar 66 is fitted over the nose portion 26 of the main body 12 with the second end 74 of the collar 66 nearest the light sources 44. The collar 66 is prevented from moving further along the end region 20 of the main body 12 by an abutment surface 75 of the main body 12.

The reflection surface 82 of the collar 66 is, therefore, located between the light sources 58 and the lens 42 in a longitudinal direction. The reflection surface 82 is substantially rear facing so that a fraction of the light that is emitted by the light sources 58 is incident on the reflection surface 82.

The cap 44 is screwed onto the nose portion 26 of the main body 12 such that the attachment portion 48 is located between the sleeve portion 68 of the collar 66 and the nose portion 26. The cap 44 is screwed onto the nose portion 26 until an end 49 of the attachment portion 48 contacts the flange 70 of the collar 66 and the flange 70 of the collar 66 is in contact with the abutment surface 75. In this way, with the collar 66 and cap 44 fully attached to the main body 12, the flange 70 is clamped between the abutment surface 75 of the main body 12 and the end 49 of the cap 44, thereby retaining the collar 66 on the main body 12. Furthermore, in this position the flange 70 extends over and covers the end 49 of the cap 44. In this way, the flange 70 blocks light emitted by the light sources 58 that would otherwise be incident on the end 49 of the cap 44.

The length of the collar 66, between the first and second ends 72, 74, is such that the first end 72 of the collar 66 does not extend beyond the front face 43 of the lens 42. In this way the collar 66 does not block the field of view of the lens 42. The collar 66 does, however, fully surround at least a part of the attachment portion 48 of the cap 44 thereby protecting this part of the cap 44 from damage.

The light sources 58 are arranged such that the centre lines 64 of the light beams 62 fall on a circle having a diameter greater than the external diameter of the collar 66. In this way, at least 50% of the light emitted by the light sources 58 passes around the collar 66 without being reflected or deflected by the reflection surface 82.

A fraction of the light emitted by each of the light sources 58 is incident on the reflection surface 82. The angle of the reflection surface 82 causes the light to be reflected in a direction away from the axis 18 of the inspection assembly 10. In particular, a fraction of the light beam 62 located between the main body 12 of the inspection assembly 10 and the centre line 64 of the light beam 62 is reflected by the reflection surface 82.

Figure 8:
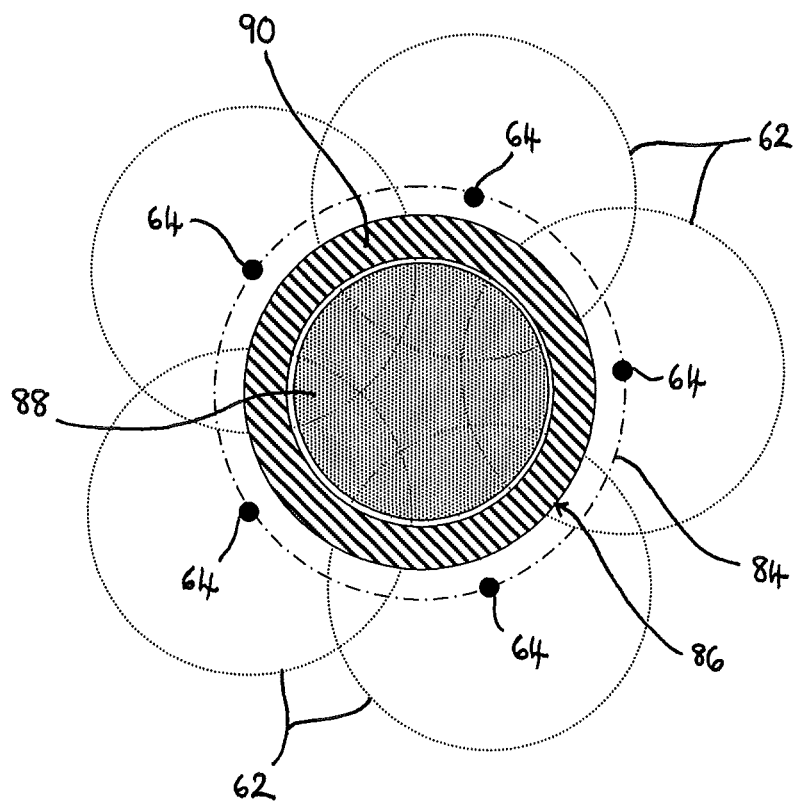
FIG. 8 illustrates an illumination pattern resulting from an annular arrangement of five light sources of the inspection assembly of FIG. 1.

This is illustrated in FIG. 8 which shows the illumination pattern resulting from an annular arrangement of five light sources emitting divergent beams of light 62. The centre line 64 of each of the beams of light 62 lies on a circle 84 having a diameter greater than the external diameter 86 of the collar. The central shaded region 88 in FIG. 8 denotes the part of each of the light beams 62 that is incident on a part of the inspection assembly 10 and does not reach the field of view of the lens 42. The hatched region 90 denotes the fraction of each of the light beams 62 that strikes the reflection surface 82 and is reflected outwardly to a peripheral region of the field of view.

It can be seen that the result of reflecting a radially inner portion 90 of each of the light beams 62 is that the overall intensity of the light in a central region of the field of view is decreased while the overall intensity of the light in a peripheral region of the field of view is increased. In this way the field of view is more evenly illuminated decreasing the likelihood that regions of an image captured by the camera will be underexposed or overexposed.

Figure 9:
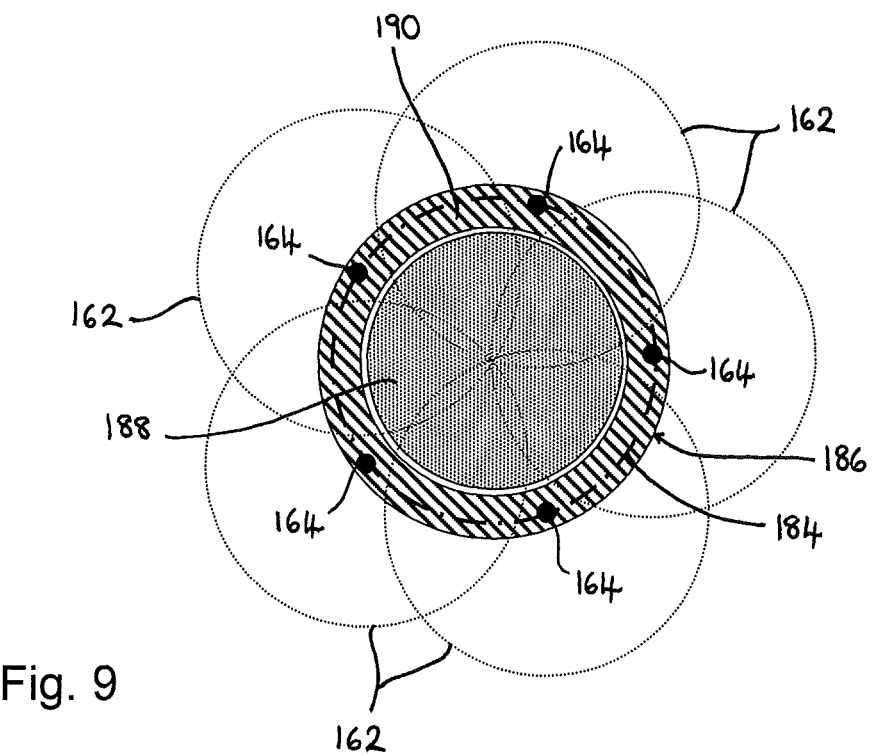
FIG. 9 illustrates an alternative illumination pattern resulting from an annular arrangement of five light sources.

In other embodiments the light sources may be arranged such that centre lines 164 of light beams 162 emitted by the light sources fall on a circle having a diameter smaller than the external diameter of the collar. This is illustrated in FIG. 9 which shows the illumination pattern resulting from an annular arrangement of five light sources emitting divergent beams of light 162. The centre line 164 of each of the beams of light 162 lies on a circle 184 having a diameter smaller than the external diameter 186 of the collar. The central shaded region 188 in FIG. 9 denotes the part of each of the light beams 162 that is incident on a part of the inspection assembly 10 and does not reach the field of view of the lens 42. The hatched region 190 denotes the fraction of each of the light beams 162 that strikes the reflection surface 82 and is reflected outwardly to a peripheral region of the field of view. In some of these embodiments at least 50% of the light emitted by the light sources 58 passes around the collar 66 without being reflected or deflected by the reflection surface 82. In one particular embodiment the diameter of the circle 184 on which the centre line 164 of each of the beams of light 162 lies is approximately 28 mm and the external diameter 186 of the collar is approximately 30 mm.

It will be appreciated that although the reflection surface 82 has been described as being part of a reflection collar 66 that is separate from the main body 12 of the inspection assembly 10, in other embodiments the reflection surface 82 may be provided on the main body 12 or may be provided by another component of the inspection assembly 10. The reflection surface may be provided on the cap.

Furthermore, in some embodiments, the collar 66 may be attached or secured directly to the main body 12 rather than being secured by means of the cap 44 as described above. Accordingly, in these embodiments the collar 66 may include means for securing the collar 66 to the main body 12, for example by means of screw threads.

It will be appreciated that it is also possible to create a more even illumination of the field of view of a lens of an inspection assembly by providing a different arrangement of light sources or by changing the pattern of light emission from the inspection assembly, compared to known camera systems.

An inspection assembly may, for example, include a first, substantially forward-facing light source or set of light sources and a second, substantially outwardly facing light source or set of light sources. In these assemblies, the first set of light sources may be oriented such that the centre line of each of the beams of light, from the first set of light sources, is at an angle of between 0° and 45° to the longitudinal axis of the assembly. The second set of light sources may be oriented such that the centre line of each of the beams of light, from the second set of light sources, is at an angle of between 30° and 90° to the longitudinal axis of the assembly and is at a greater angle than the centre lines of the first set of light sources. In this way, the second set of light sources will illuminate a peripheral region of the field of view which is only weakly illuminated or not illuminated by the first set of light sources.

In other embodiments of the inspection assembly two light sources or two sets of light sources may be provided spaced apart longitudinally along the main body of the inspection assembly. In these embodiments the angle between the centre line of each of the beams of light, from all of the light sources, and the longitudinal axis of the main body of the inspection assembly may be the same. The light source or set of lights sources further from the distal end of the main body will, however, illuminate a peripheral region of the field of view which is more weakly illuminated by the light source or set of light sources nearer the distal end.

In other embodiments only one light source or one set of lights sources may be provided; however, the light source(s) may be arranged to emit light into an end of a suitable light guide or light pipe that conveys the light to one or more windows through which the light is emitted from the inspection assembly. The light guide may comprise two or more optical fibres, a first optical fibre being arranged to emit light predominantly in a first direction from the inspection assembly and a second optical fibre being arranged to emit light predominantly in a second direction from the inspection assembly. Alternatively the inspection assembly may comprise a light pipe including a first branch and a second branch. The first branch may be arranged to emit light from the inspection assembly predominantly in a first direction and the second branch may be arranged to emit light from the inspection assembly predominantly in a second direction. In these embodiments the predominant direction of the emitted light is defined by the direction of the centre line of the beam of emitted light.

The inspection assembly of the present invention, including a reflection surface, provides an improved illumination system that may be used, in particular, with camera systems incorporating a wide angle lens.

The invention claimed is:
1. An inspection assembly comprising:
a main body having a longitudinal axis and a distal end;
an ultra wide angle lens located at the distal end, said lens having an angle of view of greater than 180°;
a light source positioned rearward of the lens to illuminate an area to be viewed beyond the distal end of the main body; and
a metal collar including a reflection surface, the reflection surface being located at a distance along the longitudinal axis between the lens and the light source, an angle between the reflection surface and the longitudinal axis of the main body being between 10° and 70°,
wherein the metal collar is a separate collar attached to the main body of the assembly, and the reflection surface is positioned such that, in use, a first fraction of the light emitted by the light source is reflected by the reflection surface before illuminating a periphery of the field of view of said lens and a second fraction of the light emitted by the light source travels to the field of view of said lens without being reflected by the reflection surface.

2. An inspection assembly as claimed in claim 1, wherein the first fraction is less than 50% of the emitted light.

3. An inspection assembly as claimed in claim 1, wherein the angle between the reflection surface and the longitudinal axis of the main body is between 30° and 40°.

4. An inspection assembly as claimed in claim 1, wherein the reflection surface is an annular surface extending around the main body.

5. An inspection assembly as claimed in claim 1, comprising a plurality of light sources positioned rearward of the lens to illuminate an area to be viewed beyond the distal end of the main body, the plurality of light sources arranged around the main body and radially outward of the lens.

6. An inspection assembly as claimed in claim 1, wherein the lens is a fish-eye lens.

7. An inspection assembly as claimed in claim 1, wherein the reflection surface is an unpolished surface of the metal collar.

8. An inspection assembly as claimed in claim 1, wherein the reflection surface is configured to cause diffuse reflection of the emitted light striking the reflection surface.

9. An inspection assembly as claimed in claim 1, further comprising an image sensor arranged to capture an image of the field of view through the lens.

10. An inspection assembly as claimed in claim 1, wherein the metal collar comprises a screw thread for securing the metal collar to the main body.

11. An inspection assembly as claimed in claim 1, further comprising a cap including an optically transparent dome-shaped window portion, said window portion extending beyond a distal end face of the main body and extending over the lens.

12. An inspection assembly as claimed in claim 11, wherein the cap comprises an attachment portion engaged with the main body to secure the cap at the distal end of the main body and a part of the metal collar is located around the attachment portion of the cap.

13. An inspection assembly as claimed in claim 11, wherein the metal collar includes a flange, and the flange extends over and covers an end of the cap to block light emitted by the light source that would otherwise be incident on the end of the cap.

14. An inspection assembly as claimed in claim 1, wherein the metal collar comprises a tubular sleeve portion, an external surface of the collar is tapered at a first end of the collar and an external surface of the collar is tapered at the second end of the collar, the tapered second end of the collar providing the reflection surface.

15. A method of inspecting a wellbore comprising:
deploying an inspection assembly along the wellbore, the inspection assembly comprising:
a main body having a longitudinal axis and a distal end; and
an ultra-wide angle lens located at the distal end, said lens having an angle of view of greater than 180°;
a metal collar including a reflection surface, the reflection surface being located at a distance along the longitudinal axis between the lens and the light source, an angle between the reflection surface and the longitudinal axis of the main body being between 10° and 70° wherein the metal collar is a separate collar attached to the main body of the assembly,
illuminating a light source positioned rearward of the lens to illuminate an area ahead of the distal end of the main body;
reflecting a first fraction of the light emitted by the light source with the reflection surface before illuminating a periphery of the field of view of said lens; and
propagating a second fraction of the light emitted by the light source to the field of view of said lens without being reflected by the reflection surface along the wellbore.

* * * * *